(12) United States Patent
Huang et al.

(10) Patent No.: US 11,580,643 B2
(45) Date of Patent: Feb. 14, 2023

(54) SYSTEM FOR FACILITATING MEDICAL IMAGE INTERPRETATION

(71) Applicant: V5 TECHNOLOGIES CO., LTD., Hsinchu (TW)

(72) Inventors: Chien-Chung Huang, Hsinchu (TW); Chien-Ting Yang, Hsinchu (TW); Tzu-Kuei Shen, Hsinchu (TW); Yu-Hsun Kao, Hsinchu (TW); Kuo-Tung Hung, Hsinchu (TW); Yueh-Heng Lee, Hsinchu (TW)

(73) Assignee: V5 TECHNOLOGIES CO., LTD., Hsinchu (TW)

( * ) Notice: Subject to any disclaimer, the term of this patent is extended or adjusted under 35 U.S.C. 154(b) by 275 days.

(21) Appl. No.: 17/039,488

(22) Filed: Sep. 30, 2020

(65) Prior Publication Data
US 2021/0366117 A1  Nov. 25, 2021

(30) Foreign Application Priority Data
May 20, 2020 (TW) .................................. 109116758

(51) Int. Cl.
*G06K 9/00* (2022.01)
*G06T 7/00* (2017.01)
(Continued)

(52) U.S. Cl.
CPC .............. *G06T 7/0014* (2013.01); *G06T 7/11* (2017.01); *G06T 11/203* (2013.01); *G16H 30/20* (2018.01);
(Continued)

(58) Field of Classification Search
CPC ....... G06T 7/0012–0016; G06T 7/0002; G06T 2210/41; G06T 2200/24; G06T 2207/30004–30104; G06T 2207/10072–10112; G06T 11/00; G06T 11/001; G06T 11/20–60; G06T 2219/004; G06T 2207/30204; G06T 2219/028; G06T 2207/20108; G06T 7/11; G06T 7/194; G06T 7/0014; G06T 2207/20112;
(Continued)

(56) References Cited

U.S. PATENT DOCUMENTS

| 2008/0155468 A1* | 6/2008 | Rosander ............... G16H 30/40 715/810 |
| 2013/0051646 A1* | 2/2013 | Nakano .................. G16H 40/63 382/131 |

(Continued)

*Primary Examiner* — Atiba O Fitzpatrick
(74) *Attorney, Agent, or Firm* — Muncy, Geissler, Olds & Lowe, P.C.

(57) ABSTRACT

A system for facilitating medical image interpretation includes a processing unit and a display control unit. The processing unit includes a location information module generating a reference location indicator, and a feature marking module generating indication markers. The display control unit is in signal connection with the processing unit and a display device. The display control unit includes an image displaying module controlling the display device to display tissue images, and an auxiliary information displaying module controlling the display device to display, for each of the tissue images displayed by the display device, the reference location indicator and the indication markers together on the tissue image.

15 Claims, 11 Drawing Sheets

(51) Int. Cl.
 *G06T 11/20* (2006.01)
 *G16H 30/20* (2018.01)
 *G06T 7/11* (2017.01)

(52) U.S. Cl.
 CPC ............... *G06T 2207/20084* (2013.01); *G06T 2207/30024* (2013.01)

(58) Field of Classification Search
 CPC ....... G06T 2210/12; G06T 2207/20081; G06T 2207/20084; G06F 3/048–0486; G16H 30/00–40; G16H 50/20; G06V 2201/03–033; G06V 10/00; G06V 10/25; G06V 10/255; G06V 10/40–422; G06V 10/759; G06V 30/18057; G06V 30/18133–18162; G06V 30/1908; G06V 10/751; G06V 10/70; G06V 10/82; G06V 10/454; A61B 6/025; A61B 6/032–037; A61B 6/461–466
 See application file for complete search history.

(56) References Cited

U.S. PATENT DOCUMENTS

| | | | |
|---|---|---|---|
| 2013/0289405 A1* | 10/2013 | Wang | A61B 8/4281 600/440 |
| 2014/0033126 A1* | 1/2014 | Kreeger | G06T 11/003 715/833 |
| 2017/0337336 A1* | 11/2017 | Weidner | A61B 6/463 |
| 2019/0096062 A1* | 3/2019 | Westerhoff | G16H 30/20 |
| 2019/0266722 A1* | 8/2019 | Sugahara | G06T 7/11 |
| 2019/0380792 A1* | 12/2019 | Poltaretskyi | A61B 34/25 |
| 2020/0261046 A1* | 8/2020 | Arai | A61B 6/488 |
| 2020/0411173 A1* | 12/2020 | Mansi | G16H 10/20 |
| 2021/0157464 A1* | 5/2021 | Innanje | G06T 7/0014 |
| 2021/0304363 A1* | 9/2021 | Makihira | G06T 5/001 |

\* cited by examiner

SYSTEM FOR FACILITATING MEDICAL IMAGE INTERPRETATION

CROSS-REFERENCE TO RELATED APPLICATION

This application claims priority of Taiwanese Invention Patent Application No. 109116758, filed on May 20, 2020.

FIELD

The disclosure relates to a system for presenting medical image, and more particularly to a system for facilitating medical image interpretation.

BACKGROUND

In order to diagnose an illness in a patient, a medical professional often has to study, piece by piece, a great number of medical images of computed tomography (CT) or magnetic resonance imaging (MRI) obtained from the patient. However, it may take a great amount of time for the medical professional to study the medical images even though the scope of studying may be narrowed down, based on his/her accumulated experience, to parts of the medical images corresponding to body portions which are more susceptible to the illness. In addition, it may take a great amount of time for the medical professional to locate a lesion to be treated in the patient, to mark the lesion and to measure the size of the lesion, putting an increased burden of workload for the medical professional. Under time pressure, the medical professional would be prone to making mistakes.

Recently, techniques of artificial intelligence (AI) have been applied to facilitate medical image interpretation. However, AI-assisted medical image interpretation software needs to be installed and go through learning in addition to existing image viewer software. Moreover, since the existing image viewer software and the AI-assisted medical image interpretation software are not integrated, the medical professional has to open both software at the same time so as to locate the lesion to be treated by means of comparison, resulting in inconvenience of use.

SUMMARY

Therefore, an object of the disclosure is to provide a system for facilitating medical image interpretation that can alleviate at least one of the drawbacks of the prior art.

According to the disclosure, the system is adapted to help locate, on a display device, a plurality of tissue features in a plurality of tissue images of a medical image model. The system includes a processing unit and a display control unit.

The processing unit is configured to perform analysis on the tissue images based on an execution rule set so as to recognize the tissue features. The processing unit includes a location information module and a feature marking module. The location information module is configured to operate based on a presentation rule of the execution rule set, and to generate a reference location indicator which is provided, for each of the tissue images, to be marked to indicate a relative location of the tissue image in the medical image model. The feature marking module is configured to operate based on a marking rule of the execution rule set, and to generate a plurality of indication markers which respectively correspond to the tissue images and each of which indicates whether the corresponding one of the tissue images contains a specific type of tissue feature.

The display control unit is in signal connection with the processing unit and the display device. The display control unit includes an image displaying module and an auxiliary information displaying module. The image displaying module is configured to control the display device to display the tissue images. The auxiliary information displaying module is configured to control the display device to display, for each of the tissue images displayed by the display device, the reference location indicator and the indication markers together on the tissue image, wherein the indication markers are displayed on the reference location indicator at specific positions that respectively correspond to the relative locations, among the tissue images that are sequentially arranged in the medical image model, of those of the tissue images that correspond to the indication markers so as to help a user locate the tissue features in the medical image model.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
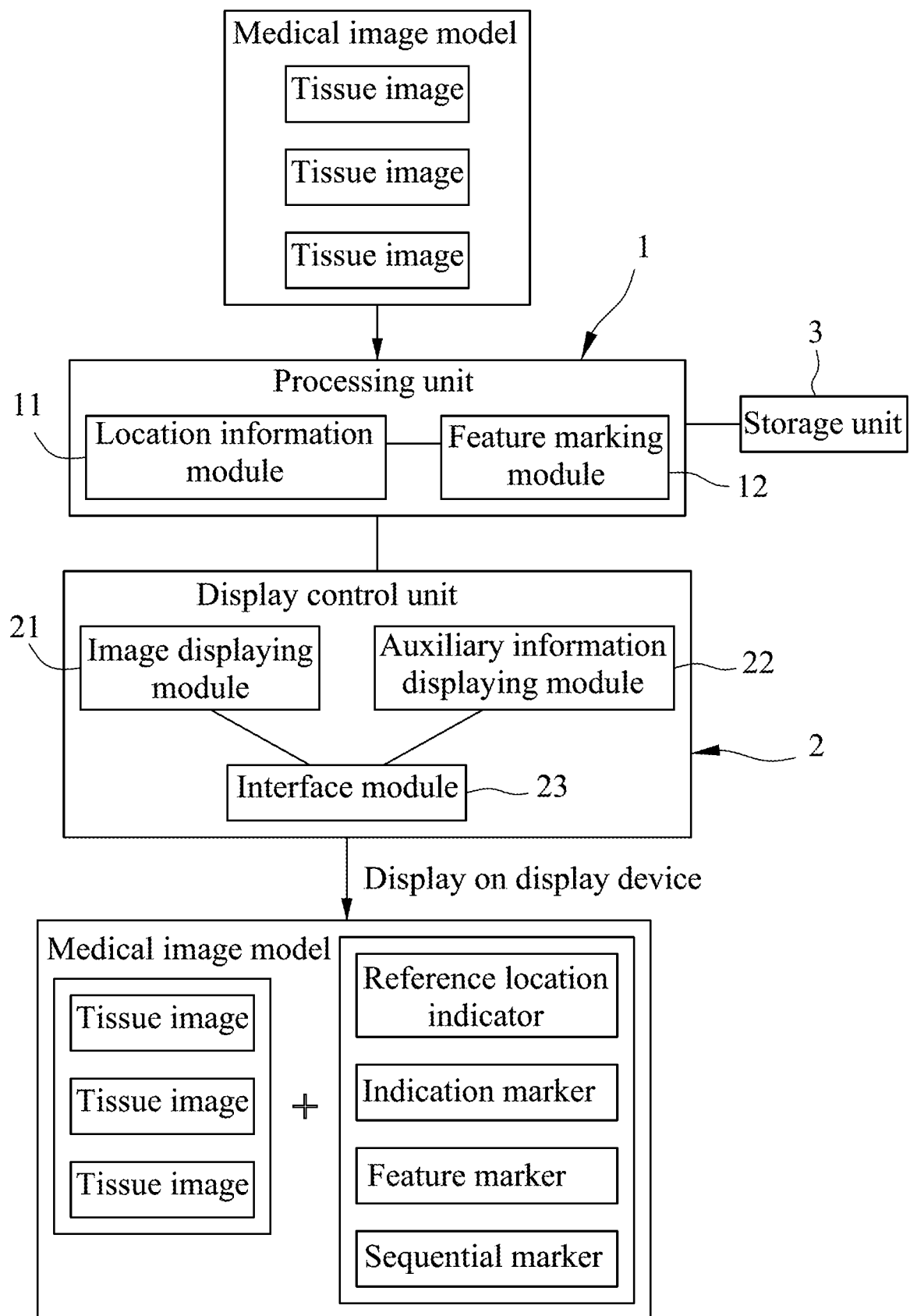
FIG. 1 is a block diagram illustrating an embodiment of a system for facilitating medical image interpretation according to the disclosure.

Referring to FIG. 1, an embodiment of a system for facilitating medical image interpretation according to the disclosure is illustrated. The system is adapted to help locate, on a display device (not shown), a plurality of tissue features in a plurality of tissue images of a medical image model. It should be noted that the tissue images of the medical image model are consecutive cross-sectional images of a scanned body part of a patient, such as a series of cross-sectional images of the lungs of the patient from top to bottom. Each of the tissue features may relate to normal tissue with no pathological change, or relate to abnormal tissue (e.g., a nodule or a cyst) where pathological changes have occurred.

In addition, transmission of the tissue images among modules/units of this system follows the standard of digital imaging and communications in Medicine (DICOM). Further, the format of the tissue images, after being processed by the system according to the disclosure, also follows the standard of DICOM. Thus, the tissue images are accessible to a user (e.g., a medical professional such as a doctor or a nurse) by using a picture archiving and communication system (PACS) or a hospital information system (HIS), and are viewable using image viewer software the user is familiar with.

The system includes a processing unit 1, a display control unit 2 and a storage unit 3. The display control unit 2 is in signal connection with the processing unit 1 and the display device. The storage unit 3 is in signal connection with the processing unit 1.

It should be noted that the processing unit 1, the display control unit 2 and the storage unit 3 may individually be implemented by one of hardware, firmware, software, and any combination thereof. For example, the processing unit 1, the display control unit 2 and the storage unit 3 may be implemented to be software modules in a program, where the software modules contain codes and instructions to carry out specific functionalities, and can be called individually or together to perform operations of the system of this disclosure.

The storage unit 3 is configured to store a plurality of feature criteria that respectively correspond to a plurality of types of tissue feature, and a plurality of sensitivity criteria each of which corresponds to sensitivity of tissue feature recognition in the tissue images.

The processing unit 1 is configured to automatically perform analysis on the tissue images based on an execution rule set. Specifically speaking, the processing unit 1 includes a location information module 11 that is configured to operate based on a presentation rule of the execution rule set, and a feature marking module 12 that is configured to operate based on a marking rule of the execution rule set for performing recognition and marking the tissue features. In this embodiment, the processing unit 1 is configured to store a plurality of neural network models that are to be utilized to realize the marking rule and that respectively correspond to the feature criteria. The neural network models are established based on an algorithm of deep learning and have been trained in advance. It should be noted that establishment of the neural network models stored in the processing unit 1 is not limited to the disclosure herein and may vary in other embodiments.

Figure 4:
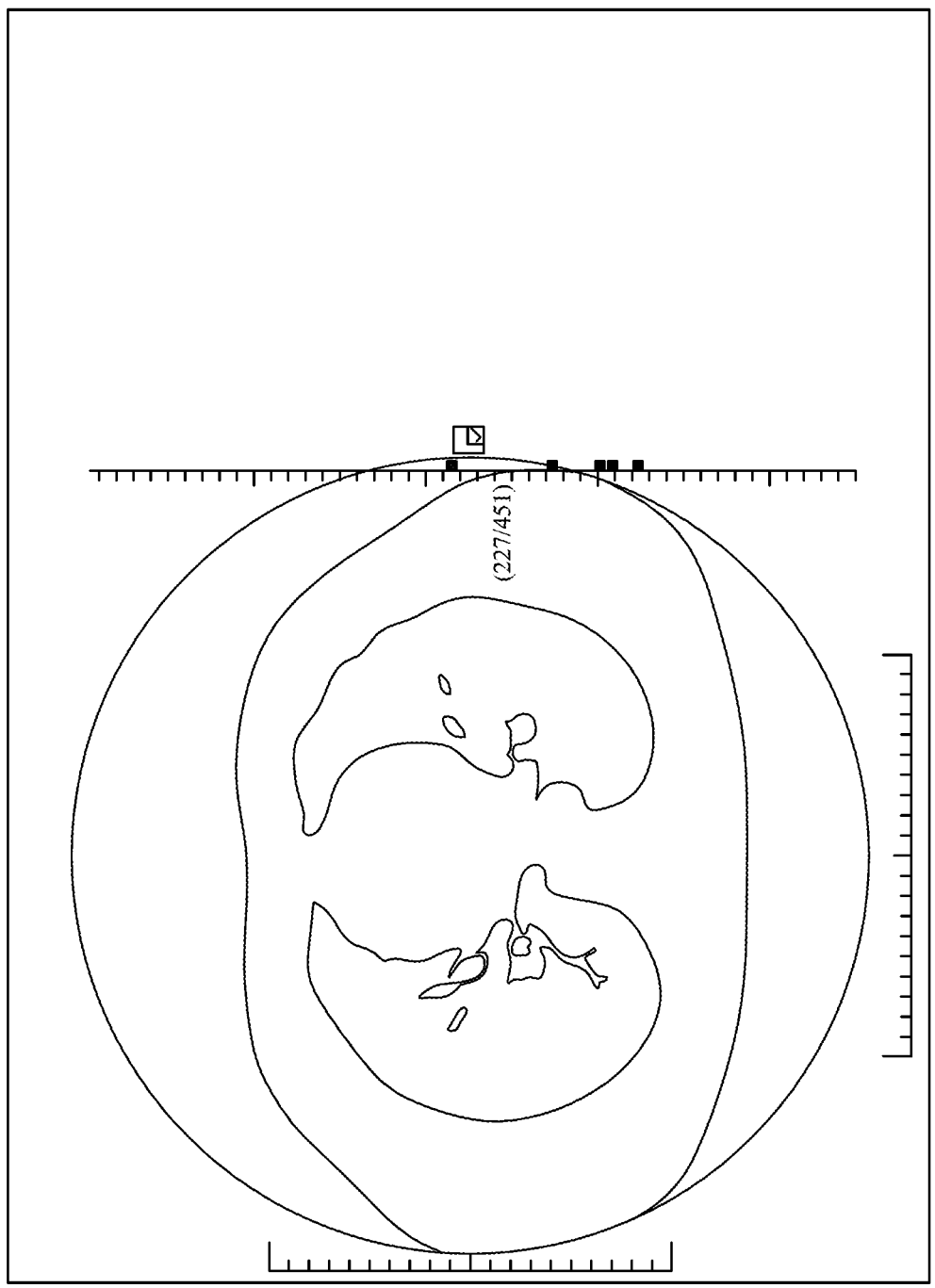
Figure 8:
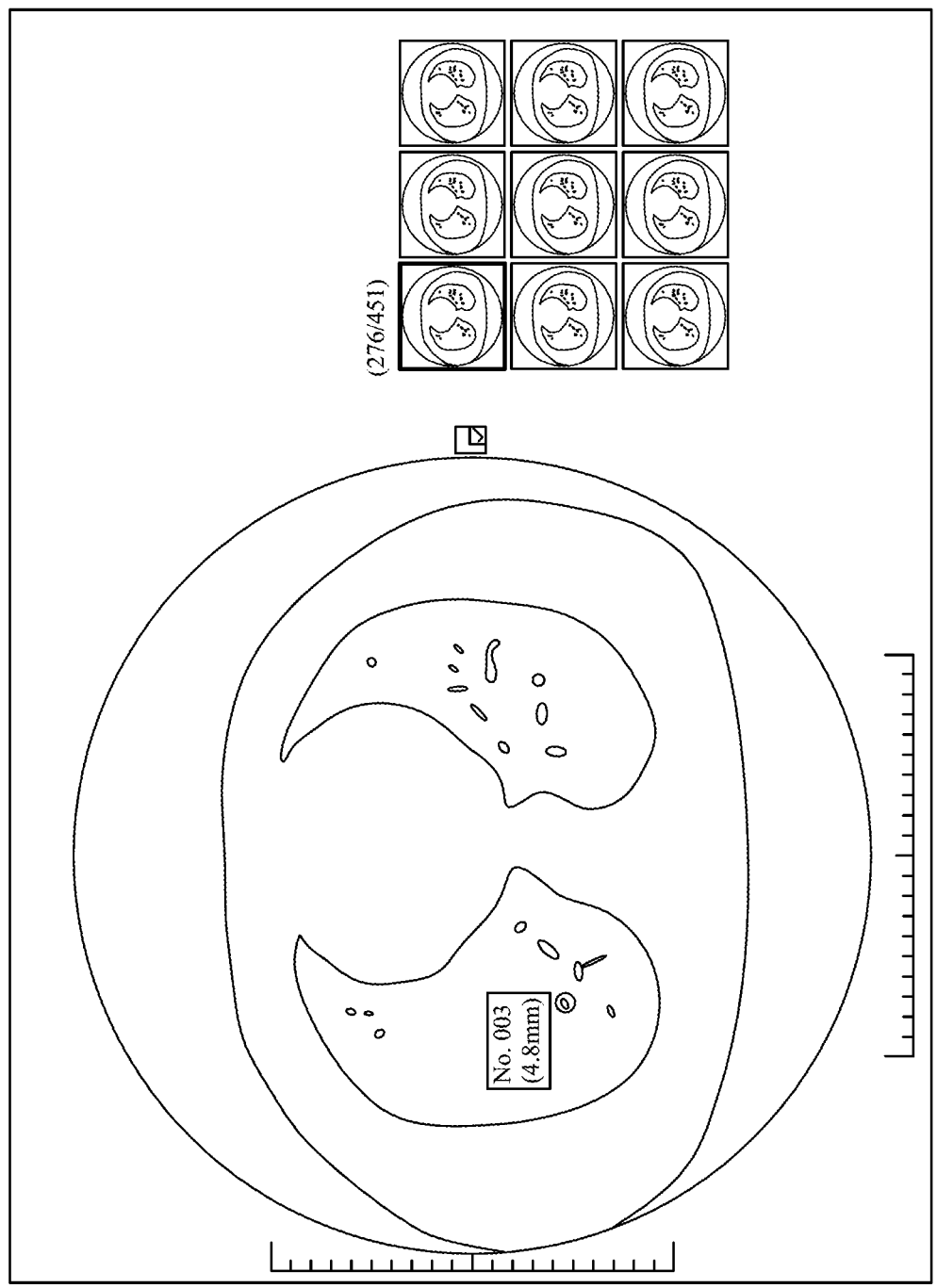
FIGS. 8 and 9 are schematic diagrams cooperatively illustrating another embodiment of presenting tissue images by the system according to the disclosure.

The location information module 11 is configured to generate a reference location indicator which is provided, for each of the tissue images, to be marked to indicate a relative location of the corresponding one of the tissue images in the medical image model. The reference location indicator may be a scale line as shown in FIG. 4, a grid as shown in FIG. 8, or a combination thereof. However, the form and representation of the reference location indicator are not limited to the disclosure herein and may vary in other embodiments. In one embodiment, both the scale line and the grid are provided, serving together as the reference location indicator. It is worth to note that transmission of the reference location indicator also follows the standard of DICOM.

The location information module 11 is further configured to generate a plurality of sequential markers which respectively correspond to the tissue images and which are related to an order in which the tissue images are sequentially arranged in the medical image model. In this embodiment, each of the sequential markers contains text information which indicates a serial number of a respective one of the tissue images and the total number of the tissue images in the medial image model, but is not limited thereto.

The feature marking module 12 is configured to generate a plurality of feature markers which respectively correspond to the tissue features, and a plurality of indication markers which respectively correspond to the tissue images and each of which indicates, on the reference location indicator, whether the corresponding one of the tissue images contains a specific type of tissue feature. In this embodiment, each of the feature markers contains text information which indicates a designated number, a size of the respective one of the tissue features, or a combination thereof. In one embodiment, for each type of tissue feature, and for each sensitivity of tissue feature recognition, the feature marking module 12 generates the indication markers which respectively correspond to the tissue images.

It is worth to note that transmission of the indication markers also follows the standard of DICOM.

Specifically speaking, for each of the feature criteria, the feature marking module 12 is configured to generate, based on the feature criterion by using the corresponding one of the neural network models, the indication markers and the feature markers all of which are related to the type of tissue feature to which the feature criterion corresponds.

For example, the storage unit 3 stores two feature criteria respectively corresponding to "nodule" and "cyst" (which are two types of tissue feature), and the processing unit 1 stores two neural network models respectively corresponding to the two feature criteria. Based on one of the two feature criteria that corresponds to the type of tissue feature "nodule" by using one of the two neural network models that corresponds to the one of the two feature criteria, the feature marking module 12 generates the indication markers and the feature markers all of which are related to the type of tissue feature "nodule". Similarly, based on the other one of the two feature criteria that corresponds to the type of tissue feature "cyst" by using the other one of the two neural network models that corresponds to the other one of the two feature criteria, the feature marking module 12 generates the indication markers and the feature markers all of which are related to the type of tissue feature "cyst".

The indication markers that are generated based on one feature criterion take a form that is different from another form of the indication markers that are generated based on a different feature criterion, and the feature markers that are generated based on one feature criterion take a form that is different from another form of the feature markers that are generated based on a different feature criterion. The form of the indication markers and the form of the feature markers may vary among different types of tissue feature to which the feature criteria correspond in the aspect of shape, color, size, line width, and/or the like. In this way, the user may be able to conveniently distinguish and recognize different types of tissue feature based on the different forms of the indication markers and the feature markers at first glance.

Additionally, for each of the sensitivity criteria, the feature marking module 12 is further configured to generate, based on the sensitivity criterion, the indication markers and the feature markers all of which are related to the tissue features recognized under the sensitivity that corresponds to the sensitivity criterion.

It is worth to note that the sensitivity of tissue feature recognition is related to a probability of recognizing a part of the tissue image as a tissue feature by the processing unit 1, and is thus positively correlated to a quantity of the indication markers and a quantity of the feature markers to be generated by the feature marking module 12. That is to say, as the sensitivity becomes higher, more tissue features would be recognized in the tissue image, and thus more indication markers and feature markers would be generated. Likewise, with a lower sensitivity, less tissue features would be recognized in the tissue image, and thus less indication markers and feature markers would be generated.

It should be noted that a higher sensitivity of tissue feature recognition is not always better. In a scenario where the sensitivity is set to be high for the type of tissue feature "nodule", the processing unit 1 may mistakenly recognize some normal tissues as a "nodule", and thus the feature marking module 12 would mistakenly generate, for such normal tissues, the indication marker and the feature marker both of which are related to the type of tissue feature "nodule". In practice, the sensitivity may be set based on past experience of using the system according to the disclosure or based on practical needs. For example, in a condition that a medical professional believes he/she would not be misled by a result of analysis provided by the system according to the disclosure even when the system operates at a high sensitivity of tissue feature recognition, or that a patient is in a special medical condition or belongs to a high-risk group of a specific disease where the tissue images need to be analyzed cautiously, the medical professional may prefer to utilize one of the sensitivity criteria that corresponds to a high sensitivity so that the medical professional would be informed of as many recognized tissue features of the type he/she is looking for as is possible based on the indication markers and the feature markers generated by the system according to the disclosure, so as to not allow any possible anomaly to pass under the radar.

A form of the indication markers that are generated based on one sensitivity criterion is different from another form of the indication markers that are generated based on a different sensitivity criterion, and a form of the feature markers that are generated based on one sensitivity criterion is different from another form of the feature markers that are generated based on a different sensitivity criterion. The form of the indication markers and the form of the feature markers may vary among different degrees of sensitivity to which the sensitivity criteria correspond in the aspect of shape, color, size, line width, and/or the like. In this way, the user may be able to conveniently distinguish and recognize different degrees of sensitivity of tissue feature recognition based on the different forms of the indication markers and the feature markers at first glance.

The display control unit 2 includes an image displaying module 21, an auxiliary information displaying module 22, and an interface module 23 which is in signal connection with the image displaying module 21 and the auxiliary information displaying module 22.

In this embodiment, the location information module 11 and the feature marking module 12 of the processing unit 1, and the image displaying module 21, the auxiliary information displaying module 22 and the interface module 23 of the display control unit 2 may individually be implemented by one of hardware, firmware, software, and any combination thereof. For example, the location information module 11, the feature marking module 12, the image displaying module 21, the auxiliary information displaying module 22 and the interface module 23 may be implemented to be software modules in a program, where the software modules contain codes and instructions to carry out specific functionalities, and can be called individually or together to perform the operations of the system of this disclosure.

The image displaying module 21 is configured to control the display device to display the tissue images.

The auxiliary information displaying module 22 is configured to control the display device to display, on each of the tissue images displayed by the display device, a corresponding one of the indication markers, a corresponding one of the sequential markers, the feature marker(s) corresponding to the tissue feature(s) in the tissue image, and the reference location indicator. The indication markers are displayed on the reference location indicator at specific positions that respectively correspond to the relative locations, among the tissues images that are sequentially arranged in the medical image model, of those of the tissue images that correspond to the indication markers so as to facilitate a user to locate the tissue features in the medical image model.

The interface module 23 is operable to, for each of the feature criteria, switch between a single-type mode and a multiple-type mode. In the single-type mode, only the indication markers and the feature markers generated based on one of the feature criteria is to be displayed. In the multiple-type mode, the indication markers and the feature markers generated based on multiple ones of the feature criteria are to be displayed at the same time.

Similarly, the interface module 23 is also operable to, for each of the sensitivity criteria, switch between a single-sensitivity mode and a multiple-sensitivity mode. In the single-sensitivity mode, only the indication markers and the feature markers generated based on one of the sensitivity criteria is to be displayed. In the multiple-sensitivity mode, the indication markers and the feature markers generated based on multiple ones of the sensitivity criteria are to be displayed at the same time.

Next, some embodiments of presenting the tissue images by the system according to the disclosure will be exemplarily described in the following for further explanation.

Figure 2:
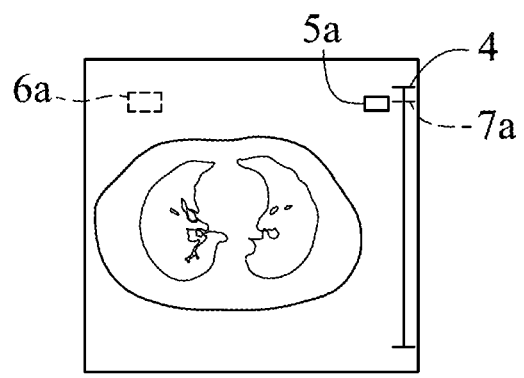
FIG. 2 is a schematic diagram illustrating an embodiment of displaying tissue images that are sequentially arranged in a medical image model and indication markers that correspond to the tissue images by the system according to the disclosure.
Figure 2:
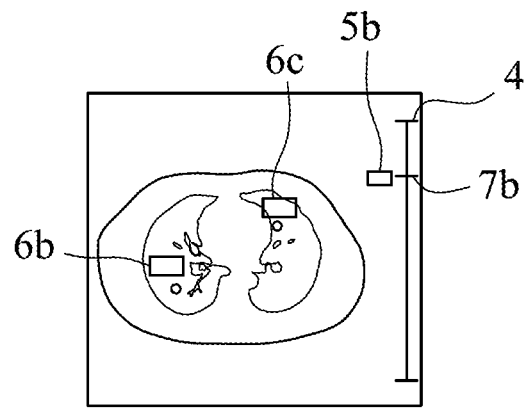
Figure 2:
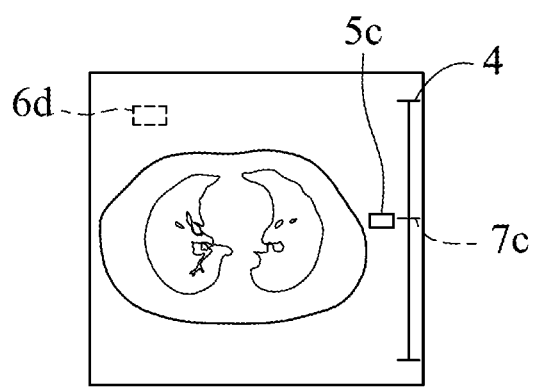
Figure 2:
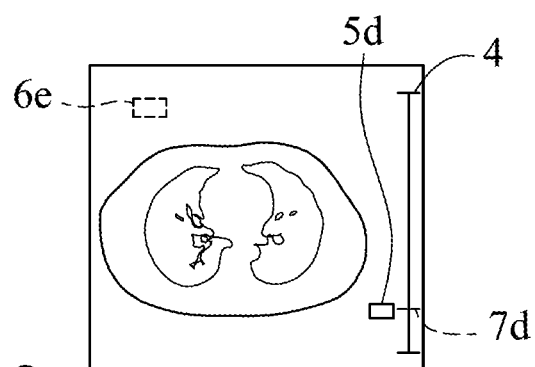

First, referring to FIGS. 1 and 2, the location information module 11 is configured to operate based on the presentation rule of the execution rule set, and to generate a reference location indicator 4 and four sequential markers (5a, 5b, 5c and 5d) which respectively correspond to four tissue images shown in FIG. 2.

In this embodiment, the reference location indicator is a scale line. For each of the four tissue images, the location information module 11 is further configured to mark, on the scale line from top to bottom, the respective one of the sequential markers around the specific position that corresponds to the relative location of the tissue image among the tissue images that are sequentially arranged in the medical image model. In this way, the user may be able to conveniently know the relative location of the tissue image among the tissue images in the medical image model by referring to the specific position on the scale line where the sequential marker is near and by reading the text information (not shown in FIG. 2) contained in the sequential marker.

Moreover, the feature marking module 12 is configured to, based on the marking rule of the execution rule set, generate four indication markers (7a, 7b, 7c and 7d) which respectively correspond to the four tissue images and each of which indicates whether the corresponding one of the tissue images contains a specific type of tissue feature (e.g., an abnormal tissue), and generate feature markers (6a, 6b, 6c, 6d and 6e) which respectively correspond to the tissue features in the four tissue images. Similarly, for each of the four tissue images, the feature marking module 12 is further configured to mark, on the scale line from top to bottom, the respective indication marker at the specific position which corresponds to the relative location of the tissue image among the tissue images that are sequentially arranged in the medical image model.

It should be noted that for each of the four tissue images, there is one indication marker, and there is one or more feature markers depending on the number of tissue feature(s) recognized by the feature marking module 12 in the tissue image, with the number of the feature marker(s) equal to the number of recognized tissue feature(s) in the tissue image. For example, referring to the second tissue image from the top of FIG. 2, the feature marking module 12 recognizes, based on the feature criterion by using the corresponding neural network model, two tissue features (which may be related to abnormal tissues where pathological changes have occurred) in the tissue image, and thus generates two feature markers (6*b* and 6*c*), correspondingly. Comparatively, for each of the remaining three tissue images in FIG. 2, the feature marking module 12 recognizes one tissue feature therein, and thus generates one feature marker (6*a*, 6*d* or 6*e*), correspondingly.

It is worth to note that FIG. 2 is an example of the multiple-type mode, and in this embodiment, the forms of the feature markers and the forms of the indication markers are differentiated (e.g., in color, in shape, in size, etc.) for different types of tissue feature. A feature marker or an indication marker is colored for a tissue feature related to an abnormal tissue (one type of tissue feature). On the other hand, a feature marker or an indication marker is colorless, and hence is invisible, for a tissue feature related to a normal tissue where no pathological change has occurred (another type of tissue feature). For example, in FIG. 2, the feature markers (6*b* and 6*c*) and the indication marker (7*b*) are colored and are illustrated with solid lines; the feature markers (6*a*, 6*d* and 6*e*) and the indication markers (7*a*, 7*c* and 7*d*) are colorless and are illustrated with dashed lines. In particular, the colored markers (i.e., the feature markers and the indication markers which are colored) may be further differentiated according to different types of tissue feature, where the different types may be different severities of pathological changes. For instance, the feature marker (6*b*) is colored red for malignant tumor (one type), and the feature marker (6*c*) is colored green for benign tumor (another type). In such case, FIG. 2 shows three types of tissue feature, namely normal tissue, malignant tumor, and benign tumor.

In one embodiment, all of the indication markers are marked together on the scale line in each of the tissue images. Consequently, the user may be able to efficiently find one(s) of the tissue images that is (are) relatively more significant (e.g., related to abnormal tissues) than others by referring to the corresponding one (s) of the indication markers that is (are) colored on the scale line while the user is viewing any one of the tissue images. For example, under this configuration, for the medical image model that contains the four tissue images as depicted in FIG. 2, the user would know that the second tissue image is related to at least one abnormal tissue when seeing that the indication marker (7*b*) on the scale line is colored when the first tissue image is displayed.

Referring to FIGS. 1, and 3 to 7, an embodiment of presenting tissue images of lungs of a patient with use of image viewer software is illustrated. The tissue images are contained in a medical image model that is established by using chest computer tomography (CT). It should be noted that in other embodiments, presentation of tissue images may further include text information which indicates a medical record number, a timestamp, a body part being scanned, or the like.

Figure 3:
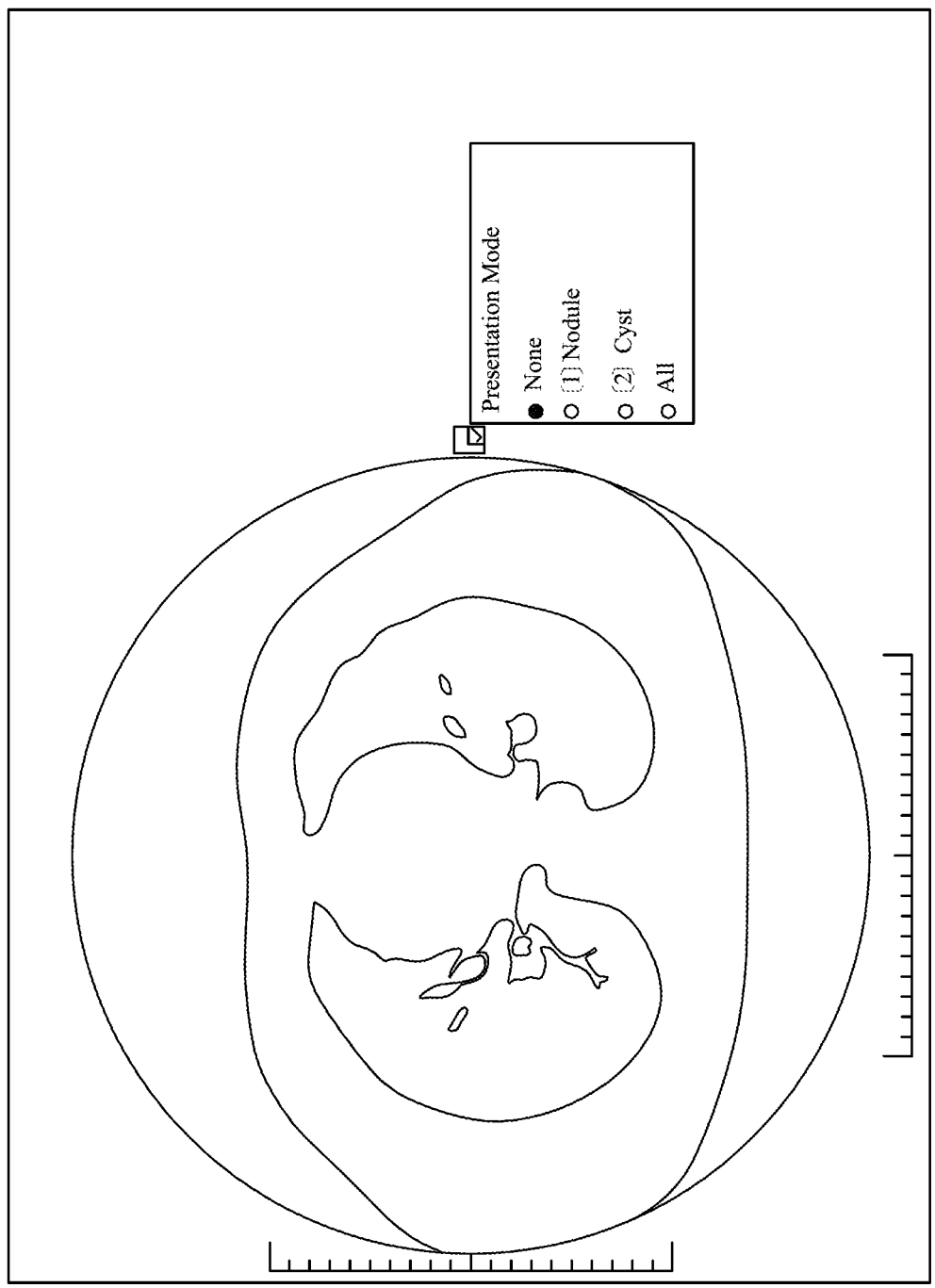
FIGS. 3 to 7 are schematic diagrams cooperatively illustrating an embodiment of presenting tissue images by the system according to the disclosure.

For each of the tissue images, the interface module 23 is operable to control the display device to display, as shown in FIG. 4, the reference location indicator (i.e., the scale line), the respective sequential marker (i.e., (227/451)"), and the indication markers (i.e., small solid rectangles) all at once, or to control the display device to refrain from displaying, as shown in FIG. 3, any one of the reference location indicator, the respective sequential marker, the feature marker(s) and the indication markers. In FIG. 4, the text information (i.e., "227/451") contained in the sequential marker (i.e., "( )") indicates that the tissue image being displayed is the 227$^{th}$ tissue image among a total of 451 tissue images.

In this embodiment, the types of tissue feature to be located are "lung nodule" and "lung cyst". The interface module 23 is operable to control the display device to make a single-type presentation, i.e., to display the feature markers and the indication markers that correspond to one of the types of tissue feature "lung nodule" and "lung cyst" (i.e., the single-type mode) or to make a multiple-type presentation, i.e., to display the feature markers and the indication markers that correspond to both types of tissue feature "lung nodule" and "lung cyst" (i.e., the multiple-type mode).

Figure 5:
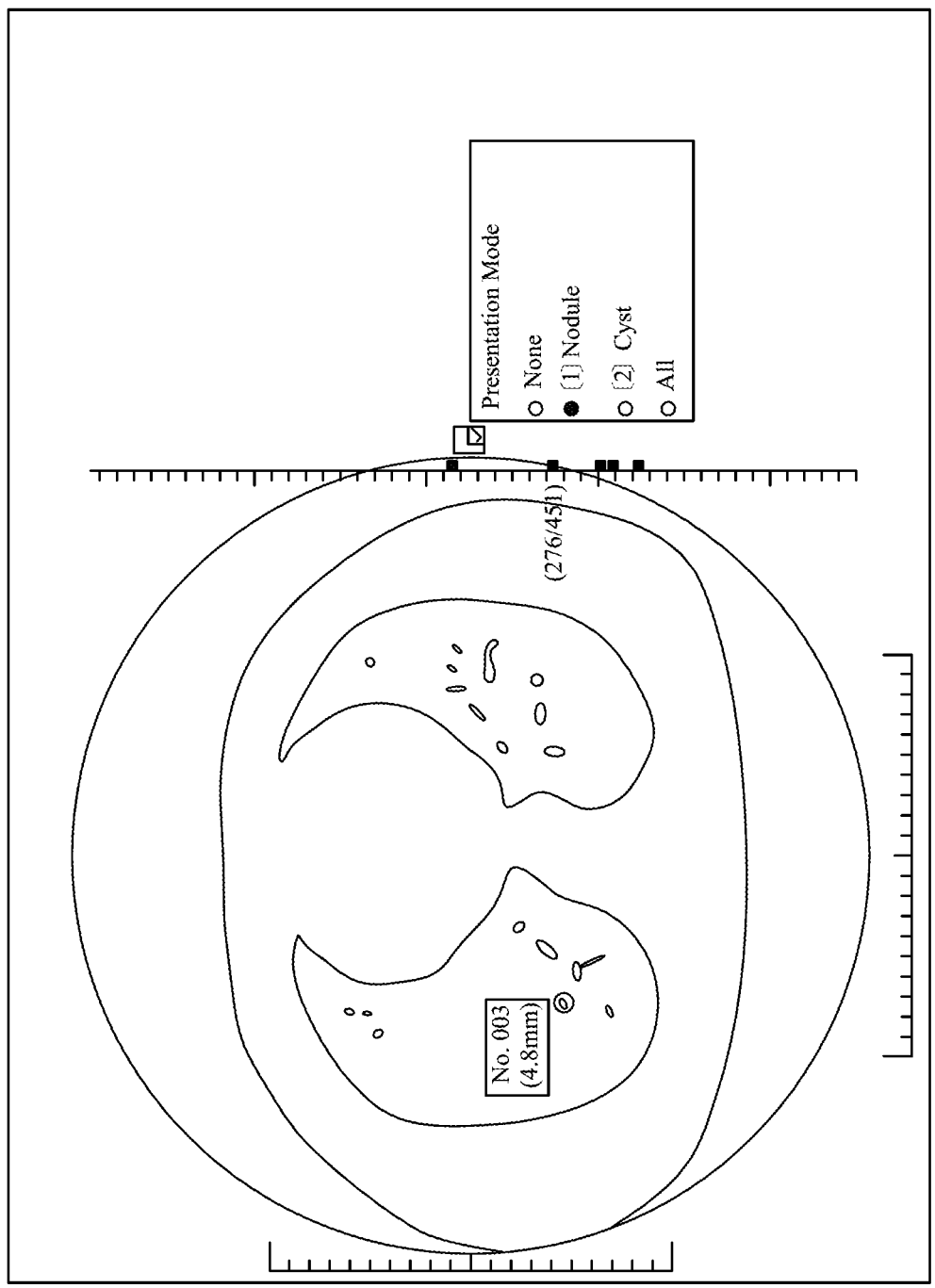

Referring to FIGS. 4 and 5, in a scenario where the display device is controlled to make a single-type presentation corresponding to the type "lung nodule" (single-type mode), the user would know that the tissue image in FIG. 4 (i.e., the 227$^{th}$ tissue image) contains no tissue feature of the type "lung nodule" because it contains no feature marker, and the user would know that the tissue image in FIG. 5 (i.e., the 276$^{th}$ tissue image) contains one tissue feature of the type "lung nodule" when seeing that one feature marker (i.e., a block containing text information "No. 003 (4.8 mm)") appears in the tissue image. By reading the text information, the user would know details of the tissue feature such as the size or the density thereof. Moreover, the user would know that most of the tissue images that contain the tissue features corresponding to the type "lung nodule" are distributed in the last half of the tissue images in terms of the sequential order by seeing the locations of the indication markers on the scale line, and would be able to retrieve any one of the tissue images containing the tissue feature (s) by referring to the indication markers marked on the scale line. That is to say, efficiency of locating the tissue features in the medical image model may be enhanced.

Figure 6:
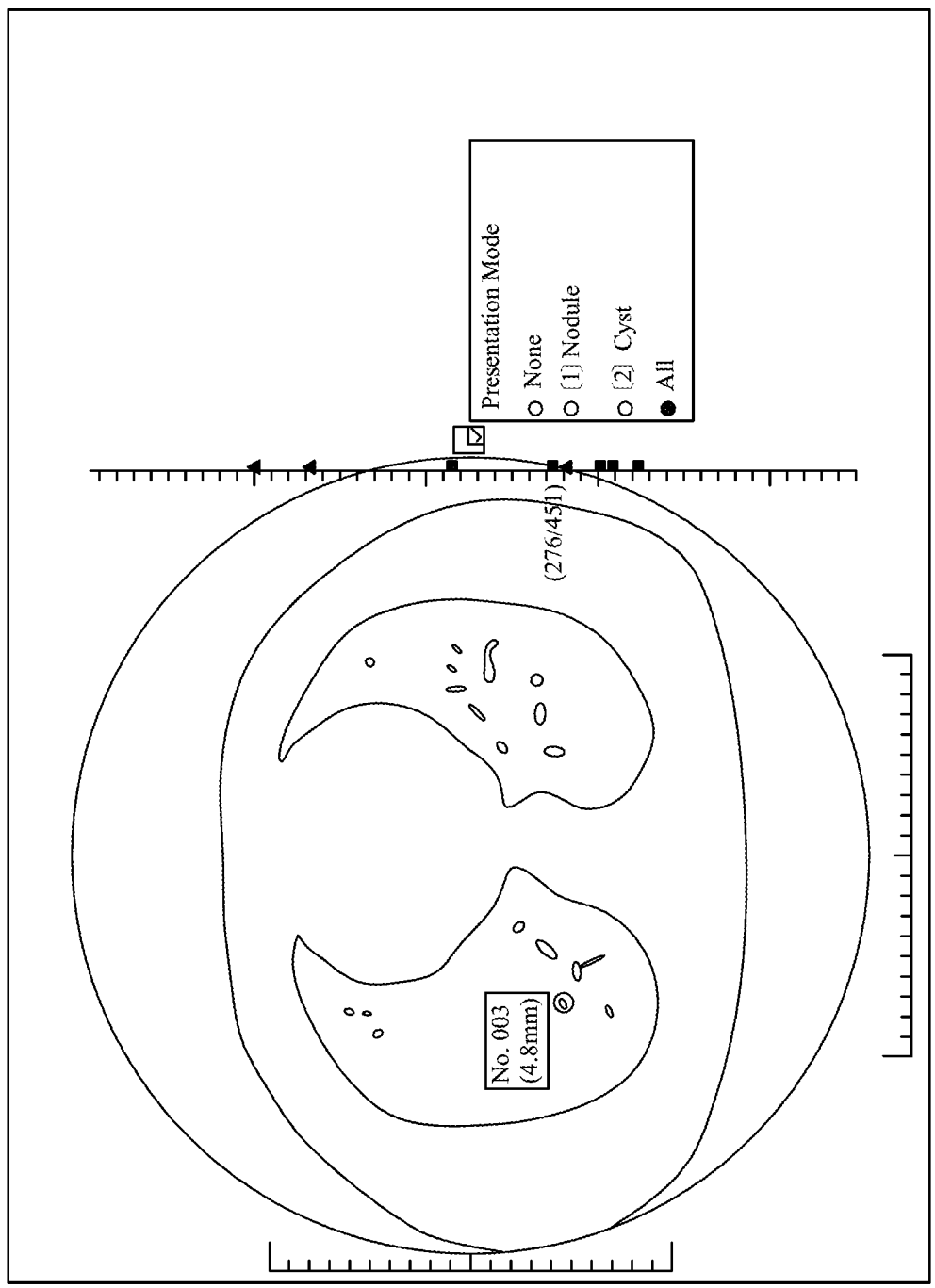

Referring to FIG. 6, in a scenario where the display device is controlled make a multiple-type presentation corresponding to both the types "lung nodule" and "lung cyst" to display all together the feature markers and the indication markers corresponding to both the types "lung nodule" and "lung cyst", the user is able to distinguish, by seeing the forms of the indication markers, which one of the tissue images contains tissue feature(s) corresponding to the type "lung nodule" and which one of the tissue images contains tissue feature(s) corresponding to the type "lung cyst". More specifically, in this embodiment, the forms of the indication markers are differentiated in shape. The shape of an indication marker corresponding to the type "lung nodule" is a rectangle, and the shape of an indication marker corresponding to the type "lung cyst" is a triangle. The legend for explanation of the indication markers is not depicted. In this way, the user would know that one of the tissue images contains tissue feature(s) corresponding to the type "lung nodule" when seeing that the indication marker corresponding to said one of the tissue images is a rectangle, and that another one of the tissue images contains tissue feature(s) corresponding to the type "lung cyst" when seeing that the indication marker corresponding to said another one of the tissue images is a triangle. Thus, efficiency of locating different types of tissue feature in the medical image model may be further enhanced.

Figure 7:
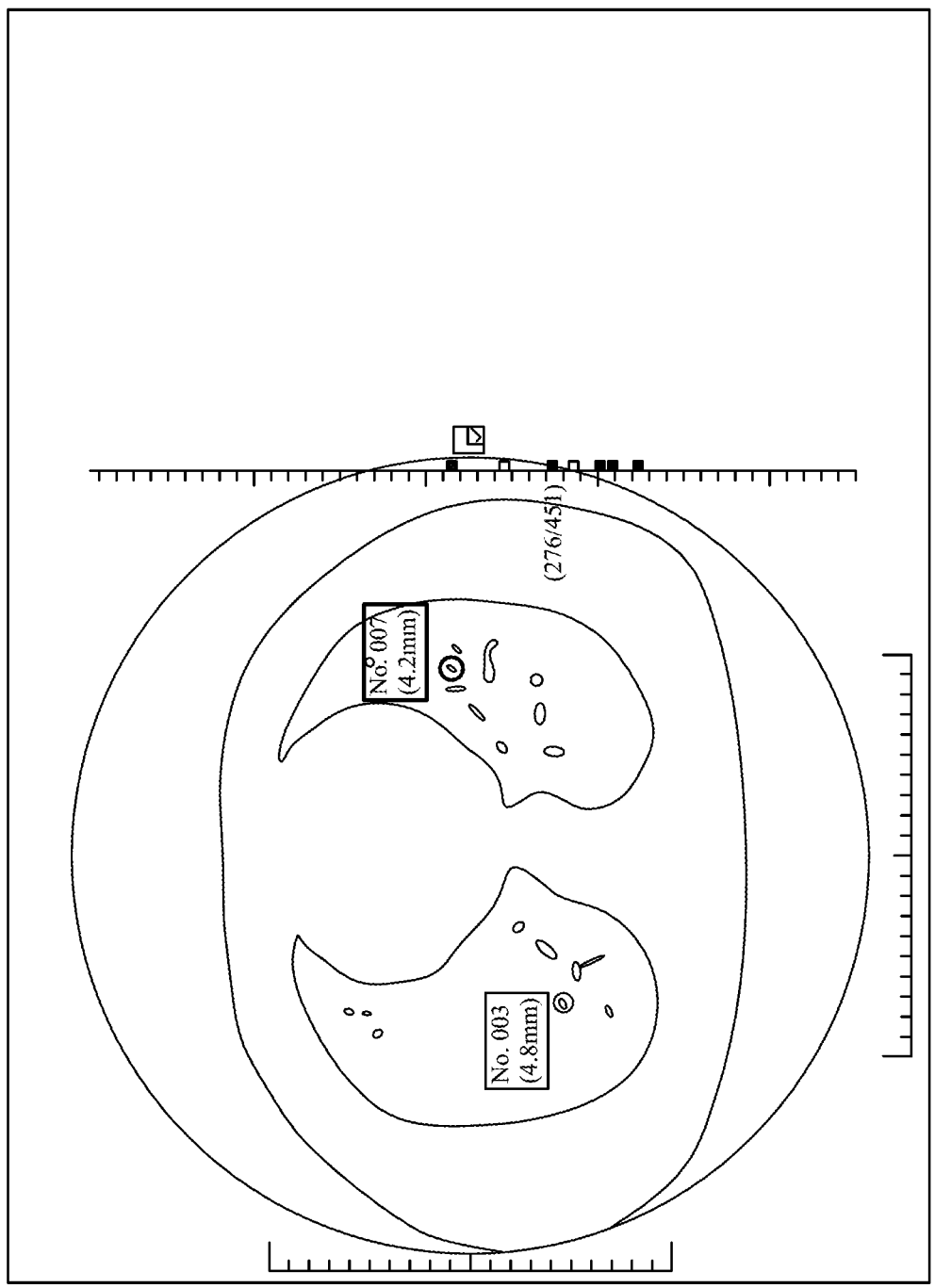

The interface module 23 is further operable to control the display device operate in the single-sensitivity mode to display the feature markers and the indication markers which correspond to one sensitivity criterion as shown in FIG. 5, or operate in the multiple-sensitivity mode to display the feature markers and the indication markers which correspond to multiple sensitivity criteria at the same time as shown in FIG. 7. More specifically, in this embodiment, the forms of the feature markers are differentiated in line width for different sensitivity criteria, and the forms of the indication markers are differentiated in color for different sensitivity criteria. For the sensitivity criterion corresponding to a low degree of sensitivity of tissue feature recognition, the feature marker is represented with a thin line, and the indication marker has a dark color (illustrated as solid rectangles). Oppositely, for the sensitivity criterion corresponding to a high degree of sensitivity of tissue feature recognition, the feature marker is represented with a thick line, and the indication marker has a light color (illustrated as hollow rectangles). In FIG. 7, the user would know that the tissue feature marked with the feature marker which indicates "No. 003 (4.8 mm)" is recognized at a low degree of the sensitivity because the feature marker is represented with a thin line, and that the tissue feature marked with the feature marker which indicates "No. 007 (4.2 mm)" is recognized at a high degree of the sensitivity because the feature marker is represented with a thick line. In this way, the user would be able to distinguish what kind of sensitivity criterion the feature marker or the indication marker corresponds to by looking at the form of the feature marker or the indication marker.

Figure 9:
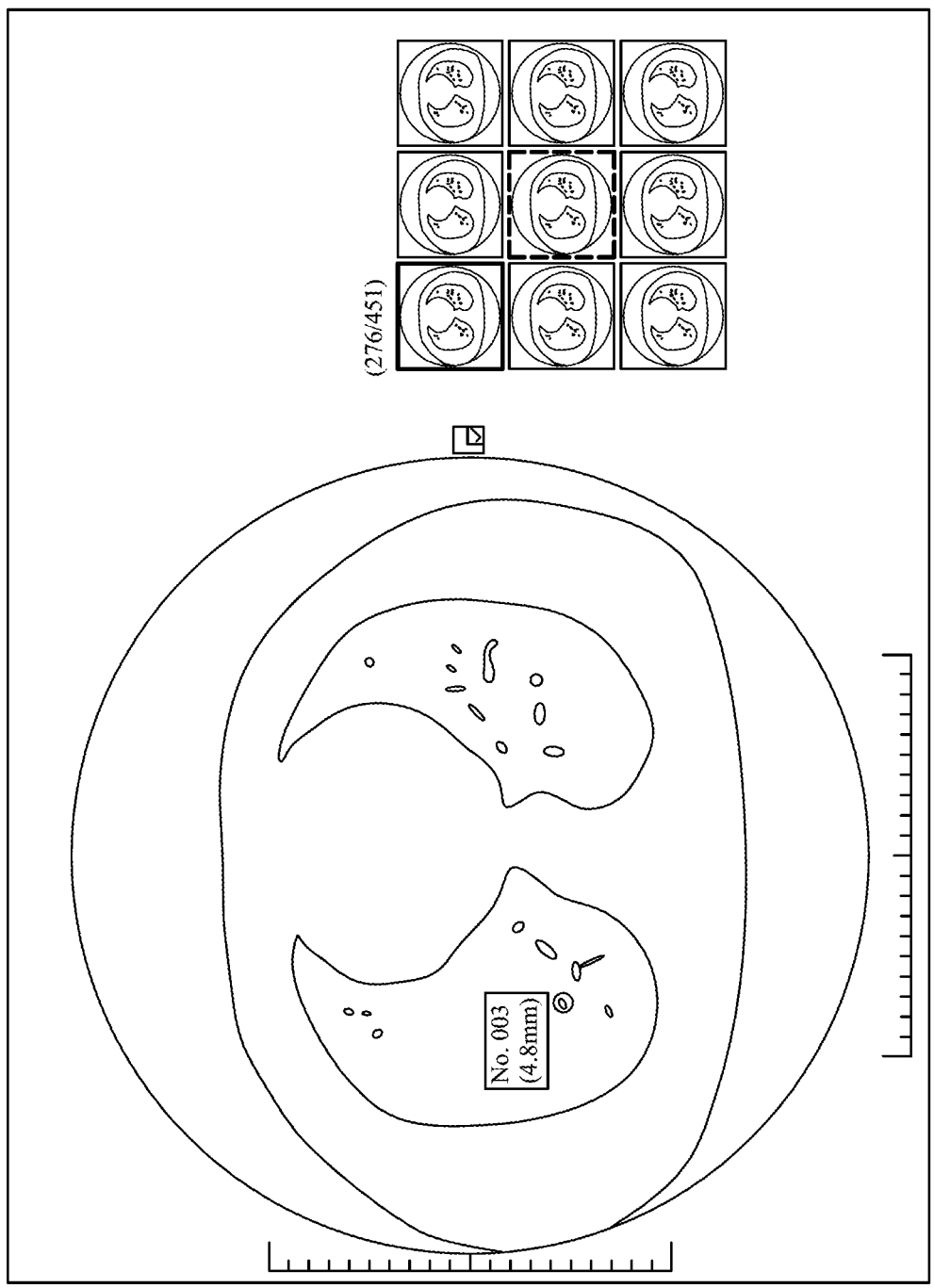

Referring to FIGS. 1, 8 and 9, another embodiment of presenting tissue images of lungs of a patient with use of image viewer software is illustrated. This embodiment is similar to the previous embodiment, but is different therefrom in that the reference location indicator is a grid. In particular, the grid has nine square regions that are arranged in an array of three rows and three columns, but arrangement of the square regions of the grid is not limited to the disclosure herein and may vary in other embodiments. Another difference from the previous embodiment is that markers relating only to a group of nine tissue images can be shown at a time.

When displaying one of the tissue images, the image displaying module 21 is configured to control the display device to display, in the square regions of the grid, a plurality of thumbnails of a group of the tissue images that includes the tissue image currently being displayed (see the left hand side of FIG. 8 or FIG. 9) and adjacent eight of the tissue images in the medical image model adjacent to the tissue image currently being displayed in terms of sequential order. For the tissue image that is currently displayed, the location information module 11 is further configured to mark, on the grid, the corresponding one of the sequential markers around the square region where the thumbnail of the tissue image is displayed. The feature marking module 12 is further configured to mark, on the grid, the indication markers that respectively correspond to the tissue images of the group on boarders of the square regions where the thumbnails of the tissue images are displayed.

Similar to the previous embodiment, the interface module 23 is operable to control the display device to operate in the single-type mode to display the feature markers and the indication markers that correspond to one of the types of tissue feature "lung nodule" and "lung cyst" as shown in FIG. 8, or to operate in the multiple-type mode to display the feature markers and the indication markers that correspond to both types of tissue feature "lung nodule" and "lung cyst" as shown in FIG. 9.

In this embodiment, the forms of the indication markers are differentiated in line pattern. The indication marker represented with a solid line corresponds to the type "lung nodule", and the indication marker represented with a dashed line corresponds to the type "lung cyst". In this way, referring to FIG. 9, the user would know, no matter which one of the tissue images is being displayed, that one of the tissue images of the group of nine tissue images contains tissue feature(s) corresponding to the type "lung nodule" when seeing that the indication marker corresponding to said one of the tissue images is marked with the solid line, and that another one of the tissue images of the group of nine tissue images contains tissue feature(s) corresponding to the type "lung cyst" when seeing that the indication marker corresponding to said another one of the tissue images is marked with the dashed line.

Figure 10:
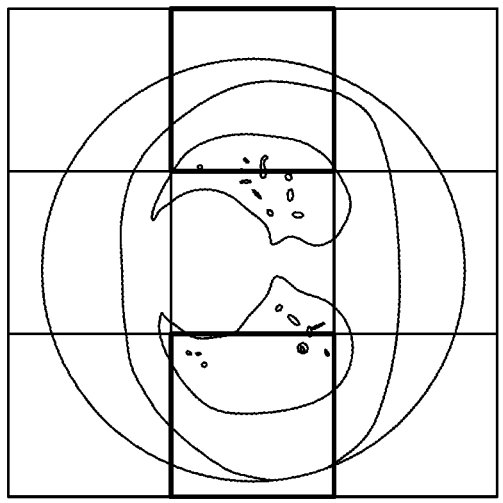
FIGS. 10 and 11 are schematic diagrams cooperatively illustrating still another embodiment of presenting tissue images by the system according to the disclosure.
Figure 10:
Figure 11:
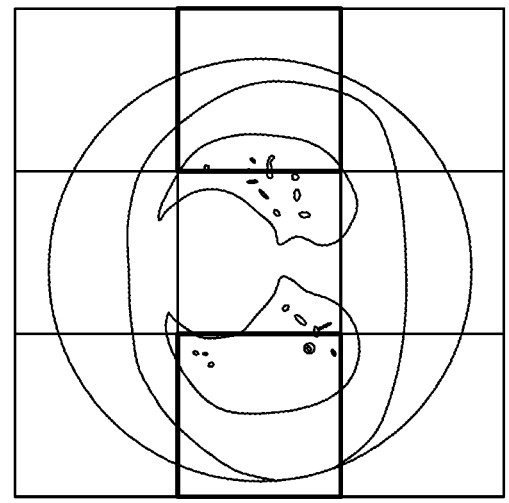
Figure 11:
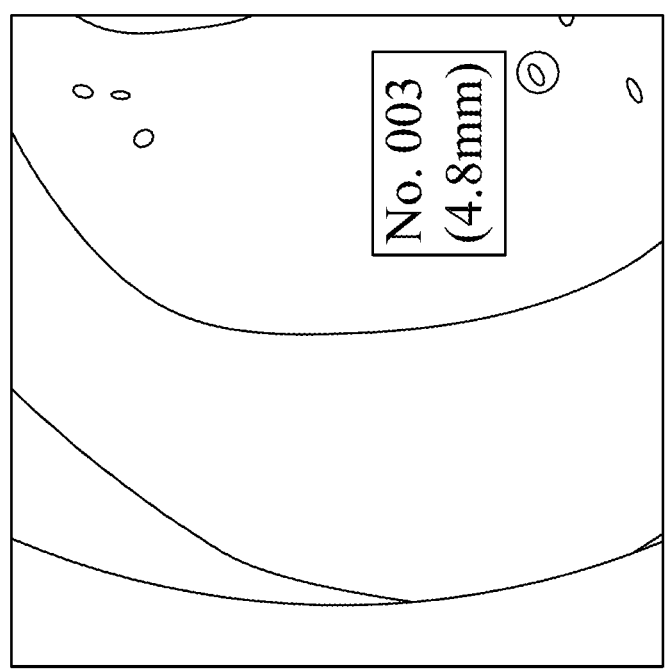

Referring to FIGS. 1, 10 and 11, still another embodiment of presenting tissue images of lungs of a patient with use of image viewer software is illustrated. This embodiment is similar to the embodiment shown in FIGS. 8 and 9, but is different therefrom in that display of anyone of the tissue images can be zoomed in, and the image displaying module 21 is configured to control the display device to display, in the square regions of the grid, a plurality of thumbnails of different divisions of the tissue image. As shown in FIG. 10, one of the divisions of the tissue image being enlarged is displayed to the left of the grid.

Similar to the previous embodiment, the forms of the indication markers are differentiated in line pattern. The indication marker represented with a solid line corresponds to the type "lung nodule", and the indication marker represented with a dashed line (no example is depicted) corresponds to the type "lung cyst". From FIG. 10, the user would know that two divisions of the tissue image contain tissue feature (s) corresponding to the type "lung nodule" when seeing that the indication markers corresponding thereto are represented with the solid line.

Conventionally, the file format of the tissue images to be analyzed by using techniques of artificial intelligence (AI) is limited to the JPEG file format or the BMP file format since image analysis by using techniques of AI (hereinafter also referred to as AI analysis) is mostly realized by utilizing off-the-shelf models that are available from shared resources and that only support the JPEG and BMP file formats. Therefore, the format of the tissue images following the standard of DICOM has to be converted into the JPEG file format or the BMP file format before undergoing the AI analysis, and reading a result of the AI analysis performed on the tissue image the format of which has been converted requires additional software other than the existing image viewer software. In addition, it is difficult to convert the JPEG format or the BMP format of the tissue images back to the format which follows the standard of DICOM. Hence, a lot of time and effort has to be spent on manually marking the tissue features, which are recognized by the AI analysis performed on the tissue images thus converted, on the tissue images that are compatible with PACS or HIS so as to allow the result of the AI analysis to be utilized in combination with the (original) tissue images.

Comparatively, by using the system according to the disclosure, auxiliary information (e.g., the feature markers, the indication markers or the like) is directly added to the tissue images having the format which follows the standard of DICOM. That is to say, tissue feature recognition and tissue feature marking are performed on the tissue images having the format which follows the standard of DICOM. Therefore, users can utilize the tissue images with existing image viewer software. That is to say, time and effort spent on processing the tissue images may be saved, and mistakes of manually marking auxiliary information on the tissue images may be avoided.

To sum up, the system for facilitating medical image interpretation according to the disclosure utilizes the location information module 11 to generate the reference location indicator and the sequential markers, utilizes the feature marking module 12 to generate the indication markers and the feature markers, utilizes the image displaying module 21 to control the display device to display the tissue images, and utilizes the auxiliary information displaying module 22 to control the display device to display, for each of the tissue images displayed by the display device, the reference location indicator, the respective sequential marker, the corresponding feature marker (s) and the indication markers together on the tissue image. In this way, medical image interpretation performed by medical professionals may be facilitated, work efficiency of medical professionals may be improved, and human error may be alleviated. Moreover, since data transmission of the system follows the standard of DICOM, medical professionals are able to use existing image viewer software to view the tissue images, and carry out medical image interpretation with the assistance of the reference location indicator, the sequential markers, the feature markers and the indication markers provided by the system, without having to open additional software other than the existing image viewer software. Therefore, convenience of use may be enhanced.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A system for facilitating medical image interpretation, adapted to help locate, on a display device, a plurality of tissue features in a plurality of tissue images of a medical image model, said system comprising:
    a processing unit configured to perform analysis on the tissue images based on an execution rule set, and comprising:
        a location information module configured to operate based on a presentation rule of the execution rule set, and to generate a reference location indicator provided, for each of the tissue images, to be marked to indicate a relative location of the tissue image in the medical image model, and
        a feature marking module that is configured to operate based on a marking rule of the execution rule set for performing recognition and marking the tissue features, and to generate a plurality of indication markers which respectively correspond to the tissue images and each of which indicates whether the corresponding one of the tissue images contains a specific type of tissue feature;
    a display control unit in signal connection with said processing unit and the display device, and comprising:
        an image displaying module configured to control the display device to display the tissue images, and
        an auxiliary information displaying module configured to control the display device to display, for each of the tissue images displayed by the display device, the reference location indicator and the indication markers together on the tissue image, wherein the indication markers are displayed on the reference location indicator at specific positions that respectively correspond to the relative locations, among the tissue images that are sequentially arranged in the medical image model, of those of the tissue images that correspond to the indication markers so as to help a user locate the tissue features in the medical image model; and
    a storage unit in signal connection with said processing unit, and configured to store a plurality of feature criteria that respectively correspond to a plurality of types of tissue feature,
    wherein for each of the feature criteria, said feature marking module is further configured to generate, based on the feature criterion, the indication markers that are related to the type of tissue feature corresponding to the feature criterion, and
    wherein said display control unit further includes an interface module that is in signal connection with said auxiliary information displaying module, and that is operable to, for each of the feature criteria, switch between a single-type mode where only the indication markers generated based on the feature criterion is to be displayed, and a multiple-type mode where the indication markers generated based on multiple ones of the feature criteria are to be displayed at the same time.

2. The system as claimed in claim 1, wherein:
    said location information module is further configured to generate a plurality of sequential markers which respectively correspond to the tissue images and which are related to an order in which the tissue images are sequentially arranged in the medical image model; and
    said auxiliary information displaying module is further configured to control the display device to display, for each of the tissue images displayed by the display device, the respective one of the sequential markers on the tissue image.

3. The system as claimed in claim 2, wherein:
    the reference location indicator is a scale line; and
    for each of the tissue images, said location information module is further configured to mark, on the scale line, the respective one of the sequential markers around the specific position that corresponds to the relative location of the tissue image among the tissue images that are sequentially arranged in the medical image model.

4. The system as claimed in claim 2, wherein:
the reference location indicator is a grid; and
when displaying one of the tissue images, said image displaying module is configured to control the display device to display, in square regions of the grid, a plurality of thumbnails of a group of the tissue images that includes the tissue image currently being displayed and adjacent ones of the tissue images in the medical image model adjacent to the tissue image currently being displayed in terms of sequential order; and
for the tissue image that is currently displayed, said location information module is further configured to mark, on the grid, the respective one of the sequential markers around the square region where the thumbnail of the tissue image is displayed.

5. The system as claimed in claim 1, wherein:
said feature marking module is further configured to generate a plurality of feature markers which respectively correspond to the tissue features; and
said auxiliary information displaying module is further configured to control the display device to display, on each of those of the tissue images displayed by the display device that contains at least one of the tissue features, the feature marker(s) corresponding to the tissue feature(s) in the tissue image.

6. The system as claimed in claim 1, wherein:
the reference location indicator is a scale line; and
for each of the tissue images, said feature marking module is further configured to mark, on the scale line, the indication markers at the specific positions which respectively correspond to the relative locations of the tissue images among the tissue images that are sequentially arranged in the medical image model.

7. The system as claimed in claim 1, wherein:
the reference location indicator is a grid; and
when displaying one of the tissue images, said image displaying module is configured to control the display device to display, in square regions of the grid, a plurality of thumbnails of a group of the tissue images that includes the tissue image currently being displayed and adjacent ones of the tissue images in the medical image model adjacent to the tissue image currently being displayed in terms of sequential order; and
for the tissue image that is currently displayed, said feature marking module is further configured to mark, on the grid, the indication markers that respectively correspond to the tissue images of the group on borders of the square regions where the thumbnails of the group of the tissue images are displayed.

8. The system as claimed in claim 1, wherein for each of the feature criteria, the indication markers that are generated based on the feature criterion take a form that is different from another form of the indication markers that are generated based on a different one of the feature criteria.

9. The system as claimed in claim 1, wherein said processing unit is further configured to store a plurality of neural network models that are utilized to realize the marking rule and that respectively correspond to the feature criteria.

10. The system as claimed in claim 1:
wherein said storage unit is further configured to store a plurality of sensitivity criteria each of which corresponds to sensitivity of tissue feature recognition in the tissue images;
for each of the sensitivity criteria, said feature marking module is further configured to generate, based on the sensitivity criterion, the indication markers that are related to the tissue features recognized under the sensitivity that corresponds to the sensitivity criterion.

11. The system as claimed in claim 10, wherein for each of the sensitivity criteria, the indication markers that are generated based on the sensitivity criterion take a form that is different from another form of the indication markers that are generated based on a different one of the sensitivity criteria.

12. The system as claimed in claim 10, wherein
said interface module is further operable to, for each of the sensitivity criteria, switch between a single-sensitivity mode where only the indication markers generated based on the sensitivity criterion is to be displayed, and a multiple-sensitivity mode where the indication markers generated based on multiple ones of the sensitivity criteria are to be displayed at the same time.

13. The system as claimed in claim 1, wherein said processing unit is further configured to store a neural network model that is utilized to realize the marking rule.

14. The system as claimed in claim 1, wherein transmission of the tissue images, the reference location indicator and the indication markers follows the standard of digital imaging and communications in Medicine (DICOM).

15. A system for facilitating medical image interpretation, adapted to help locate, on a display device, a plurality of tissue features in a plurality of tissue images of a medical image model, said system comprising:
a processing unit configured to perform analysis on the tissue images based on an execution rule set, and including
a location information module that is configured to operate based on a presentation rule of the execution rule set, and to generate a reference location indicator which is provided, for each of the tissue images, to be marked to indicate a relative location of the tissue image in the medical image model, and
a feature marking module that is configured to operate based on a marking rule of the execution rule set for performing recognition and marking the tissue features, and to generate a plurality of indication markers which respectively correspond to the tissue images and each of which indicates whether the corresponding one of the tissue images contains a specific type of tissue feature;
a display control unit in signal connection with said processing unit and the display device, and including
an image displaying module that is configured to control the display device to display the tissue images, and
an auxiliary information displaying module that is configured to control the display device to display, for each of the tissue images displayed by the display device, the reference location indicator and the indication markers together on the tissue image, wherein the indication markers are displayed on the reference location indicator at specific positions that respectively correspond to the relative locations, among the tissue images that are sequentially arranged in the medical image model, of those of the tissue images that correspond to the indication markers so as to help a user locate the tissue features in the medical image model; and
a storage unit in signal connection with said processing unit, and configured to store a plurality of sensitivity criteria each of which corresponds to sensitivity of tissue feature recognition in the tissue images,
wherein for each of the sensitivity criteria, said feature marking module is further configured to generate, based on the sensitivity criterion, the indication markers that are related to the tissue features recognized under the sensitivity that corresponds to the sensitivity criterion, and wherein said display control unit further includes an interface module that is in signal connection with said auxiliary information displaying module, and that is operable to, for each of the sensitivity criteria, switch between a single-sensitivity mode where only the indication markers generated based on the sensitivity criterion is to be displayed, and a multiple-sensitivity mode where the indication markers generated based on multiple ones of the sensitivity criteria are to be displayed at the same time.

\* \* \* \* \*